(12) United States Patent
Myeong et al.

(10) Patent No.: US 7,959,656 B2
(45) Date of Patent: *Jun. 14, 2011

(54) ADIPOSE RESOLVE APPARATUS FOR LOW-POWER LASER

(75) Inventors: Hyeon Seong Myeong, Seoul (KR); Chul Gyu Lee, Seoul (KR)

(73) Assignee: YOLO Medical Inc., Surrey, B.C. (CA)

( * ) Notice: Subject to any disclaimer, the term of this patent is extended or adjusted under 35 U.S.C. 154(b) by 324 days.

This patent is subject to a terminal disclaimer.

(21) Appl. No.: 11/577,356

(22) PCT Filed: Feb. 28, 2006

(86) PCT No.: PCT/KR2006/000694
§ 371 (c)(1),
(2), (4) Date: Apr. 17, 2007

(87) PCT Pub. No.: WO2006/093384
PCT Pub. Date: Sep. 8, 2006

(65) Prior Publication Data
US 2008/0114418 A1 May 15, 2008

(30) Foreign Application Priority Data

Mar. 2, 2005 (KR) .................... 10-2005-0017330
Feb. 17, 2006 (KR) .................... 10-2006-0015778

(51) Int. Cl.
*A61B 19/00* (2006.01)
(52) U.S. Cl. ................ 607/88; 607/89; 606/10
(58) Field of Classification Search .............. 607/88–91, 607/96; 606/3, 8–12, 131
See application file for complete search history.

(56) References Cited

U.S. PATENT DOCUMENTS 4,905,690 A  3/1990  Ohshiro et al.
(Continued)

FOREIGN PATENT DOCUMENTS

KR  20-270882  4/2002
(Continued)

OTHER PUBLICATIONS

Neira et al., Plastic and Reconstructive Surgery, Sep. 1, 2002—"Fat Liquefaction : Effect of Low Level Laser Energy on Adipose Tissue", Cosmetic, pp. 912-922.

(Continued)

*Primary Examiner* — Ahmed M Farah
(74) *Attorney, Agent, or Firm* — Fulwider Patton LLP

(57) ABSTRACT

Provided is a lipolysis device using a low power laser, and more particularly, to a lipolysis device using a low power laser capable of non-invasively irradiating skin with a laser beam which may or may not be condensed through a lens or transparent window to obtain the same effect as lipolysis of adipose tissue exposed through incision using a conventional ultrasonic or low power laser. In addition, the lipolysis device includes a vacuum suction means to readily discharge liquefied fat discharged from an adipose cell and concentrated in a space between cell tissues through the groin area, where lymphatic vessels are abundant, and out of the body. Further the lipolysis device can stably contact human skin to break down fat and thus is convenient to use. Furthermore, the lipolysis device can break down subcutaneous fat by irradiating an abdominal region with a low power laser without skin damage or surgical operation, thereby effectively removing abdominal fat.

5 Claims, 12 Drawing Sheets

U.S. PATENT DOCUMENTS

| | | | |
|---|---|---|---|
| 4,930,504 A * | 6/1990 | Diamantopoulos et al. | 607/88 |
| 5,150,704 A | 9/1992 | Tatebayashi et al. | |
| 5,409,482 A * | 4/1995 | Diamantopoulos | 606/13 |
| 5,474,528 A | 12/1995 | Meserol | |
| 5,755,752 A | 5/1998 | Segal | |
| 5,879,376 A | 3/1999 | Miller | |
| 6,063,108 A | 5/2000 | Salansky et al. | |
| 6,074,411 A | 6/2000 | Lai et al. | |
| 6,106,516 A | 8/2000 | Massengill | |
| 6,273,884 B1 | 8/2001 | Altshuler et al. | |
| 6,273,885 B1 | 8/2001 | Koop et al. | |
| 6,322,584 B2 * | 11/2001 | Ingle et al. | 607/96 |
| 6,605,079 B2 | 8/2003 | Shanks et al. | |
| 6,746,473 B2 | 6/2004 | Shanks et al. | |
| 6,887,260 B1 | 5/2005 | McDaniel | |
| 7,033,381 B1 * | 4/2006 | Larsen | 607/88 |
| 2001/0011585 A1 * | 8/2001 | Cassidy et al. | 165/46 |
| 2004/0006378 A1 | 1/2004 | Shanks et al. | |
| 2004/0116984 A1 * | 6/2004 | Spooner et al. | 607/88 |
| 2005/0203594 A1 | 9/2005 | Lim et al. | |
| 2006/0095099 A1 | 5/2006 | Shanks et al. | |
| 2006/0206176 A1 | 9/2006 | Shanks et al. | |
| 2008/0108982 A1 * | 5/2008 | Barolet et al. | 606/9 |

FOREIGN PATENT DOCUMENTS

| | | |
|---|---|---|
| KR | 20-274266 | 5/2002 |
| KR | 20-302173 | 1/2003 |
| KR | 1020030000151 | 1/2003 |

OTHER PUBLICATIONS

Neira et al., Plastic and Reconstructive Surgery, Sep. 1, 2002—"Fat Liquefaction: Effect of Low Level Laser Energy on Adipose Tissue", Discussion, pp. 923-925.

* cited by examiner

ADIPOSE RESOLVE APPARATUS FOR LOW-POWER LASER

CROSS-REFERENCE TO RELATED APPLICATIONS

The present application claims priority from Korean Patent Application No. 10-2005-0017330, filed on Mar. 2, 2005, and Korean Patent Application No. 10-2006-0015778, filed on Feb. 17, 2006, which are incorporated herein by reference in the entirety.

BACKGROUND

The present invention relates to a lipolysis device using a low power laser, and more particularly, to a lipolysis device using a low power laser capable of non-invasively irradiating skin with a laser beam which may or may not be condensed through a lens or transparent window to obtain the same effect as lipolysis of adipose tissue exposed through incision using a conventional ultrasonic or low power laser. In addition, the lipolysis device includes a vacuum suction means to readily discharge liquefied fat discharged from an adipose cell and concentrated in a space between cell tissues through the groin area, where lymphatic vessels are abundant, and out of the body. Further the lipolysis device can stably contact human skin to break down fat and thus is convenient to use. Furthermore, the lipolysis device can break down subcutaneous fat by irradiating an abdominal region with a low power laser without skin damage or surgical operation, thereby effectively removing abdominal fat.

Generally, an apparatus for generating a low power laser includes a laser diode for emitting a laser having an output of 5 mW~10 mW and a wavelength of 635 nm~650 nm, and a low power laser diode driver for arbitrarily adjusting the amount of laser beam emitted from the laser diode.

Various apparatuses for obtaining a curative effect by irradiating spots on the body with a low power laser suitable for acupuncture or infected parts of the body. For example, Korean Utility Model No. 302173 discloses an electric mat for uniformly emitting a laser beam through a low power laser diode. Korean Utility Model No. 270882 discloses a waist belt including a laser generator having a laser diode for emitting laser light having a wavelength of 580~980 nm to stimulate the lumbar, thereby performing finger-pressure treatment and therefore medical treatment of a disc. Korean Utility Model No. 274266 discloses a laser for medical treatment and an LED blanket capable of widening a curative range, for example, irradiation of spots on the body suitable for acupuncture, chronic article rheumatism, frozen shoulder, lumbago, cervical vertebral sprain, gout, wrench, bruising, arthritis, stress gastritis, and so on. Korean Patent No. 457964, issued to the present applicant, discloses a laser beam radiator capable of non-invasively irradiating blood in a blood vessel with a laser beam according to a position and a thickness of the blood vessel by adjusting a distance of the laser beam condensed through an optical lens, activating metabolism of a cell by stimulating a blood cell using a laser beam, increasing formation of capillary vessels to improve blood circulation, and increasing speed of tissue treatment to activate living organisms.

While another laser apparatus using a laser beam disposed in an array for providing use convenience is proposed to be adapted to various soft materials such as a chair, a hat, a bed, a belt, and so on, when the laser beam is disposed in the soft materials in an array, a red laser capable of being output appropriately to non-invasively break down fat (about, more than 30 mW) should be used. However, since the red laser requires a separate radiation structure, there is no way of breaking down fat by non-invasively irradiating a human body.

Meanwhile, in order to effectively treat obesity using a laser, Neira, et al. discloses a new suction lipectomy capable of liquefying fat during suction lipectomy using a low power laser [PLASTIC AND RECONSTRUCTIVE SURGERY, Sep. 1, 2002—Fat liquefaction: Effect of low-level laser energy on adipose tissue].

Neira, et al.'s paper is based on a test in which lasers having a wavelength of 635 nm, an output of 10 mW, and a total energy of $1.2 \text{ J/cm}^2$, $2.4 \text{ J/cm}^2$ and $3.6 \text{ J/cm}^2$ are radiated onto adipose tissue extracted from 12 healthy women. As a result of the test, 4 minutes after laser exposure, 80% of the fat in the adipose cells is discharged, and 6 minutes after the laser exposure, 99% is discharged. Then, the discharged fat is gathered in a space between the adipose tissues.

FIG. 1 is an electron microscope photograph of a normal adipose cell at a magnification of 190, FIG. 2 is an electron microscope photograph of an adipose cell after irradiation by a low power laser for 4 minutes, at a magnification of 190, and FIG. 3 is an electron microscope photograph of an adipose cell after irradiation by a low power laser for 6 minutes, at a magnification of 190. As clearly shown in FIG. 1, generally, the normal adipose cell has a shape like a cluster of grapes. When the normal adipose cells are irradiated by the low power laser for 4 minutes, as shown in FIG. 2, some adipose cells discharge liquefied fat and lose their circular appearance. Portions designated by arrows in FIG. 2 represent fat particles discharged from the adipose cells. When irradiated for 6 minutes, such variations are generated by most adipose cells, and therefore, as shown in FIG. 3, there is no adipose cell maintaining its original appearance, all reduced to liquefied fat. Portions designated by arrows in FIG. 3 represent fat discharged from the adipose cells.

It was reported that energy of the low power laser acts to open a cell wall to discharge fat from the interior to the exterior of the adipose cell.

Using the fat liquefaction effect of the red laser on the basis of the test, suction lipectomy using a laser, in which the human body is irradiated from outside to break down fat and discharge the broken down fat from the body using a cannula (fine pipe), has been proposed.

Various methods of non-invasively irradiating skin covering a fatty area of a treatment target with a red laser beam to break down the fat of the adipose cells have been attempted. In order to irradiate a wider area for a short time, a device for forming a red laser beam with a line shape to scan the treatment target has been developed and put on the market. However, it is difficult to input a power of 10 mW and an energy density of $3.6 \text{ J/cm}^2$ required for lipolysis in the human body, thereby obtaining little practical effect.

BRIEF SUMMARY

The present invention solves aforementioned problems associated with conventional devices by providing a lipolysis device using a low power laser capable of non-invasively irradiating skin with a laser beam which may or may not be condensed through a lens or transparent window to obtain the same effect as lipolysis of adipose exposed through incision using a conventional ultrasonic or low power laser.

It is another aspect of the present invention to provide a lipolysis device using a low power laser including a vacuum suction means to readily discharge liquefied fat discharged from an adipose cell and concentrated in a space between cell tissues through the groin area, where lymphatic vessels are abundant, and out of the body.

In an exemplary embodiment of the present invention, a lipolysis device using a low power laser includes: a laser generator having a printed circuit board (PCB) provided with a power connector, a contact plate formed of a hard plate corresponding to the PCB and having a plurality of transparent windows or lenses uniformly disposed at one side surface, and a plurality of laser diodes inserted into the respective transparent windows or lenses disposed on the contact plate and electrically connected to the PCB; and a frame for accommodating the laser generator therein, in close contact with the skin, wherein the skin is irradiated with the low power laser to break down subcutaneous fat.

Each laser generated from the laser generator may have an output of 10 mW~100 mW.

In this process, the contact plate may further include a heat dissipating plate for dissipating heat generated from the laser diode.

In addition, the contact plate may be bent to have an oval surface suitable for contact with the skin, and the frame for accommodating the contact plate may be bent to have an oval surface corresponding to the contact plate.

Meanwhile, the frame may have grips formed at appropriate places on one or both sides thereof.

Alternatively, other frames may be connected to hinges pivotally installed at both ends of the frame, respectively.

In another exemplary embodiment according to the present invention, a lipolysis device using a low power laser includes: a laser generator having a printed circuit board (PCB) provided with a power connector, a contact plate corresponding to the PCB and having a plurality of transparent windows or lenses uniformly disposed at one side surface, and a plurality of laser diodes inserted into the respective transparent windows or lenses disposed on the contact plate and electrically connected to the PCB; a frame for accommodating the laser generator therein; and a vacuum suction means having a shape conforming to a shape of the frame, disposed at a front surface of the frame, and having a suction port, a vacuum line connected to the suction port through a vacuum suction part, and a vacuum pump connected to the vacuum line, thereby being in contact with the skin, wherein the lipolysis device is suctioned to the skin and then the skin is irradiated with the low power laser to break down subcutaneous fat.

The vacuum suction means may be detachably connected to the frame.

In addition, the contact plate may be flexible.

In still another exemplary embodiment according to the present invention, a lipolysis device using a low power laser includes: a vacuum suction means having a suction port, a vacuum line connected to the suction port through a vacuum suction part, and a vacuum pump connected to the vacuum line, a coupling part having a coupling hole projecting from an upper center of the vacuum suction means by a predetermined extent; and a laser generating module having a PCB connected to the vacuum suction means to receive power through a cable, a laser diode electrically connected to the PCB, a transparent window or lens appropriately installed adjacent to the laser diode, upper and lower fixtures that are mutually detachable and accommodate the PCB, the laser diode, and the transparent window or lens, and a cover installed outside of the upper and lower fixtures, wherein the lipolysis device is suctioned to the skin, and then the skin is irradiated with the low power laser to break down subcutaneous fat and stimulate a scalp to accelerate hair growth.

The upper and lower fixtures may have male and female threads threadedly engaged with each other at its lower periphery and its upper periphery, respectively, a hooking threshold may be formed at an appropriate place at an inner periphery of the upper fixture to be engaged with the PCB, and a groove may be formed at an appropriate place at a lower inner periphery of the lower fixture to be engaged with the transparent window or lens.

Alternatively, the suction port may have a manual negative pressure release hole formed at an appropriate location thereon for manually releasing vacuum pressure or negative pressure in the suction port.

In addition, the suction port may have an annular insertion groove formed at its end, and balls may be rotatably inserted into the insertion groove.

Meanwhile, the vacuum suction part may include a one-way valve.

The lipolysis device may be operated in a rhythm mode in which air in the suction port is repeatedly sucked out through the vacuum suction part at predetermined intervals, or a uniform mode in which air is continuously sucked out of the suction port, as set by a user.

Meanwhile, the vacuum suction means having the laser generating module may include a relay, formed at an appropriate location thereon, branching off into a plurality of connection vacuum lines connected to the vacuum suction part, and each of the connection vacuum lines may be connected to another vacuum suction means having a laser generating module through a vacuum suction part.

Alternatively, one connection vacuum line of the connection vacuum lines branching off from the relay may be connected to the vacuum pump, and another connection vacuum line may be connected to another relay.

As can be seen from the foregoing, the lipolysis device using a low power laser in accordance with the present invention is capable of non-invasively irradiating skin with a laser beam through a lens or transparent window by condensing the laser beam or as they are to obtain the same effect as lipolysis of adipose exposed through incision using a conventional ultrasonic or low power laser, though a laser irradiation treatment method is changed to the non-invasive method using transmission characteristics of the laser, including a vacuum suction means to readily discharge liquefied fat discharged from an adipose cell and concentrated to a space between cell tissues through the groin region, in which lymphatic vessels are abundant, to outside the body, stably contacting with human skin to break down fat to provide user convenience.

In addition, the lipolysis device using a low power laser has advantages of breaking down and liquefying subcutaneous fat by irradiating an abdominal region with a low power laser to discharge the subcutaneous fat from the body without skin damage or surgical operation, unlike conventional suction lipectomy, thereby effectively removing abdominal fat.

Furthermore, the lipolysis device using a low power laser includes a vacuum suction means for readily discharging liquefied fat, discharged from an adipose cell, concentrated to a space between cell tissues, and suctioned to the outer skin, through the groin region, in which lymphatic vessels are abundant, outside the body, thereby maximizing lymph drainage of naturally discharging excessive fat in the human body to easily cure abdominal obesity, without using an invasive discharge means such as suction lipectomy.

BRIEF DESCRIPTION OF DRAWINGS

The above and other features of the present invention will be described with reference to certain exemplary embodiments thereof illustrated the attached drawings in which.

DESCRIPTION OF MAJOR SYMBOLS IN THE ABOVE FIGURES

Figure 1:
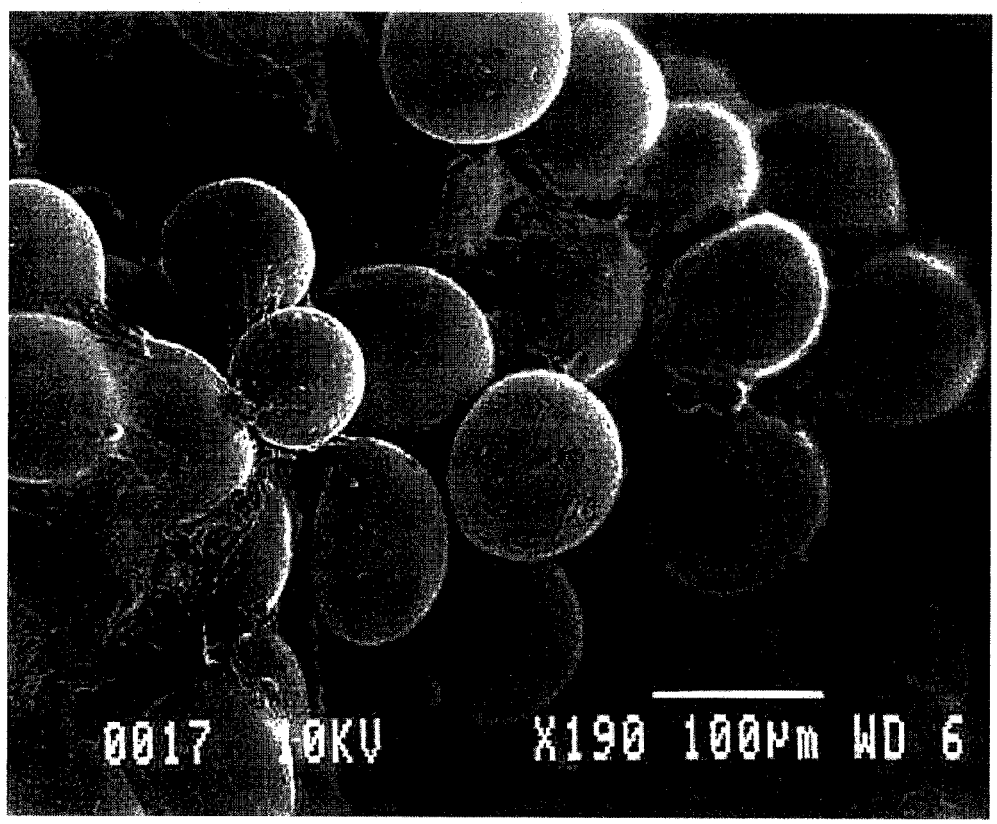
FIGS. 1 to 3 are photographs showing the appearance of fat broken down by irradiating an adipose tissue extracted from the human body with a low power laser.
Figure 2:
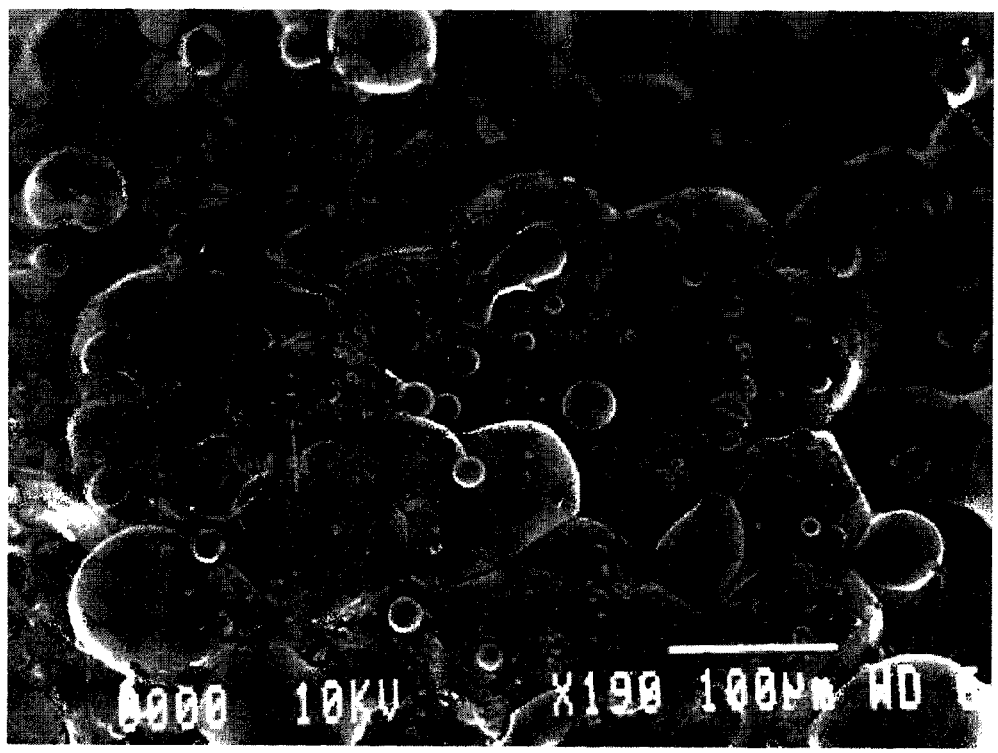
Figure 3:
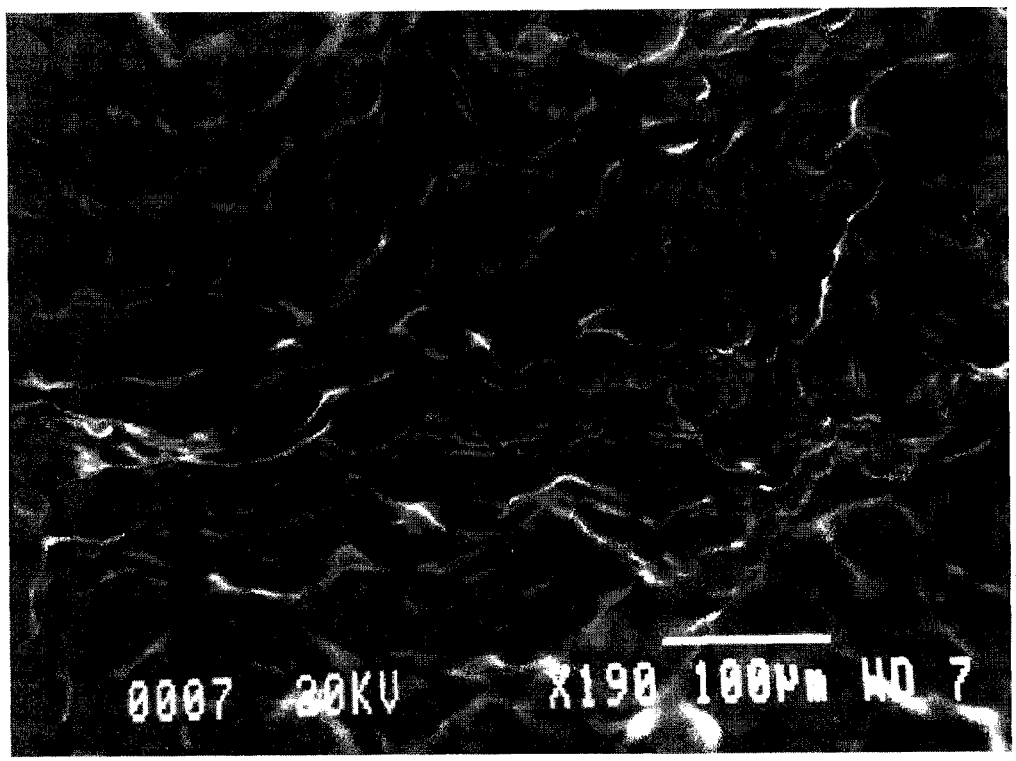

1: Lipolysis device using a low power laser
10: Laser generating unit
11: Power connector
12, 71: PCB
13, 73: Transparent window or lens
14: Contact Terminal
15, 72: Laser diode
16: Fastening bolt
17a, 17b: Fastening hole
30, 30': Frame
31: Grip
33: Hinge
35: Positioning means
50: Vacuum suction means
51: Suction port
52: Coupling hole
53: Female threaded part
54, 93: Vacuum suction part
55: One-way valve
56: Vacuum line
57: Vacuum pump
58: Manual negative pressure release hole
58a: Insertion hole
58b: ball
59: Coupling part
70: Laser generating module
71a: Cable
74: Upper fixture
74a: Male threaded part
74b: Hooking threshold
75: Lower fixture
75a: Female threaded part
75b: Groove
76: Cover
76a: Insertion hole
76b: Male threaded part
90, 90': Relay
91: Connection vacuum line
95: Vacuum pump

DETAILED DESCRIPTION

The present invention will now be described more fully hereinafter with reference to the accompanying drawings, in which preferred embodiments of the invention are shown.

Figure 4:
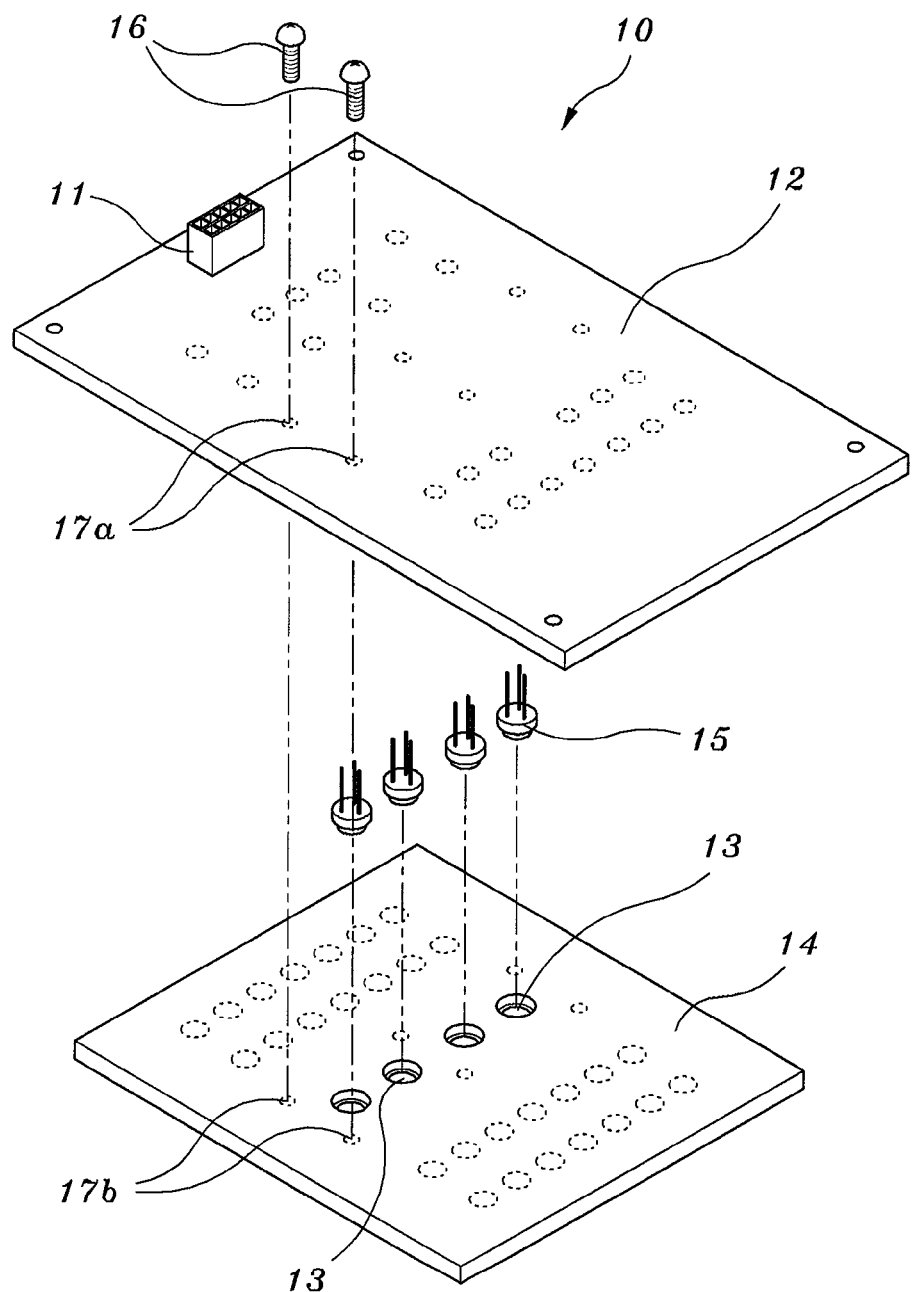
FIG. 4 is an exploded perspective view of a laser generating unit of a lipolysis device using a low power laser in accordance with the present invention.
Figure 5:
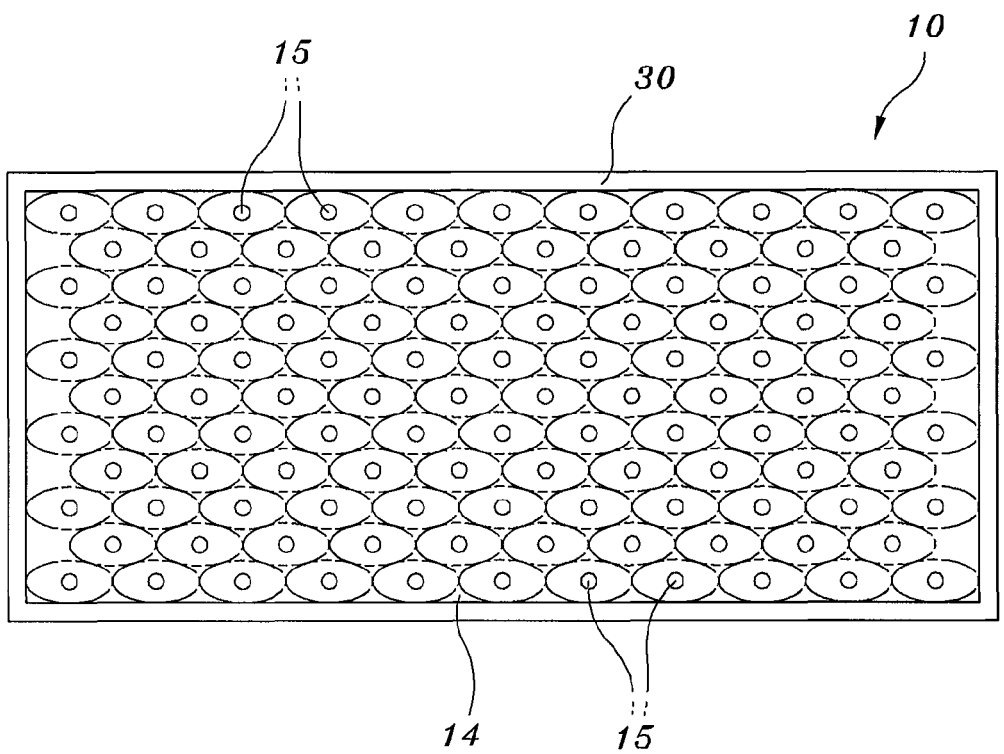
FIG. 5 a view of a laser irradiation distribution range of a lipolysis device using a low power laser in accordance with the present invention.
Figure 6:
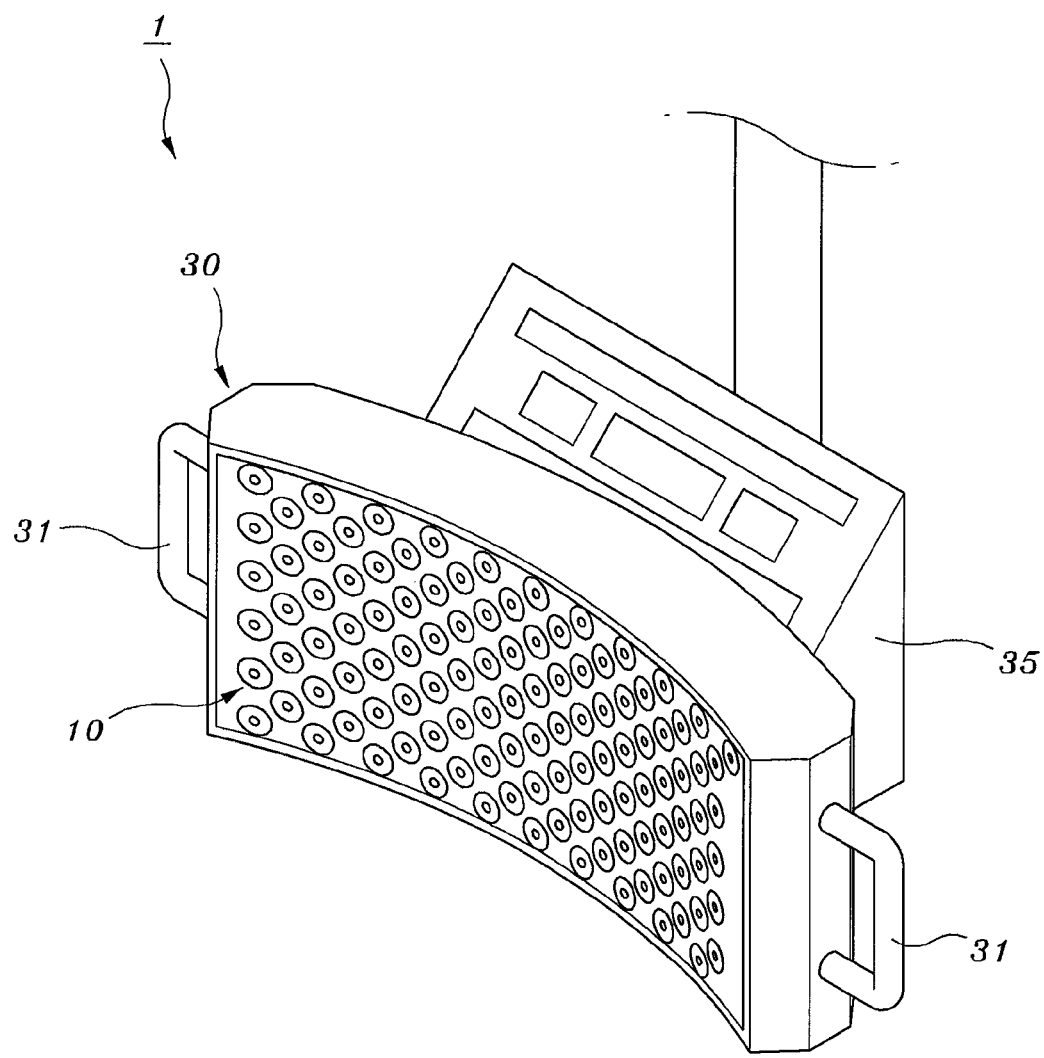
FIG. 6 is a perspective view of a lipolysis device using a low power laser in accordance with the present invention.

FIG. 4 is an exploded perspective view of a laser generating unit of a lipolysis device using a low power laser in accordance with the present invention, FIG. 5 is a view of a laser irradiation distribution range of a lipolysis device using a low power laser in accordance with the present invention, and FIG. 6 is a perspective view of a lipolysis device using a low power laser in accordance with the present invention.

As shown, a lipolysis device 1 using a low power laser in accordance with the present invention includes a laser generating unit 10 and a frame 30.

The laser generating unit 10 includes a printed circuit board (PCB) 12 provided with a power connector 11 for receiving power, a contact plate 14 corresponding to the PCB 12 and having a plurality of transparent windows or lenses 13 disposed on its one surface at predetermined intervals, and a plurality of laser diodes 15 inserted into the respective transparent windows or lenses 13 disposed on the contact plate 14 and electrically connected to the PCB 12.

The frame 30 is formed to accommodate the laser generating unit 10 therein. In this process, the laser generating unit 10 is accommodated in a front surface of the frame 30 to irradiate the skin of a user with a laser beam.

Meanwhile, a plurality of fastening holes 17a and 17b are formed at appropriate locations on the contact plate 14 to fasten the PCB 12 to the contact plate 14 by means of a plurality of fastening bolts 16. Specifically, the plurality of laser diodes 15 are installed at the PCB 12, the plurality of fastening holes 17a and 17b are formed at appropriate locations on the contact plate 14 and the PCB 12 to fasten the PCB 12 to the contact plate 14 after inserting the laser diodes 15 into the transparent windows or lenses 13 of the contact plate 14, and then, the fastening bolts 16 are fastened through the fastening holes 17a and 17b, thereby securely fastening the PCB 12 to the contact plate 14.

In addition, the plurality of lenses or windows 13 are preferably disposed at the contact plate 14 in an array, and the number of laser diodes 15 corresponding to the number of the lenses or windows 13 disposed at the contact plate 14 are preferably inserted into the lenses or transparent windows 13.

While the plurality of lenses or transparent windows 13 disposed at the contact plate 14 are uniformly disposed in the embodiment of the present invention, providing that the laser is radiated to readily break down subcutaneous fat of a user after contact with the skin, the lenses or transparent windows 13 may be irregularly disposed at the contact plate 14.

In this process, the contact plate 14 may have various shapes such as circular, rectangular, and so on.

Meanwhile, each laser generated from the laser generating unit 10 has a low output of 10 mW~100 mW. That is, in order to break down subcutaneous fat by irradiating the skin of a user with a laser beam, each laser generated from the laser diodes 15 of the laser generating unit 10 has a low output of 10 mW~100 mW, in consideration of attenuation in the human body.

As described above, each laser generated from the laser generating unit 10 has a low output of 10 mW~100 mW, the laser generating unit 10 has a plane array structure in close contact with the user's skin, and a plurality of laser diodes 15 apply lasers, respectively, thereby ensuring invasive force into the user's skin and enabling the laser to be uniformly radiated onto a larger area of the skin to simultaneously break down subcutaneous fat.

For this purpose, preferably, the contact plate 14 has a curved surface to be in smooth contact with the skin in an area such as the abdomen, in which subcutaneous fat is concentrated, and the frame 30 for accommodating the contact plate 14 also has a curved surface conforming to a shape of the contact plate 14.

While the contact plate 14 in accordance with an embodiment of the present invention has a curved surface, it may be formed of a flexible material to conform to various parts of the user's body.

In addition, the contact plate 14 in contact with the user's skin may be formed of a hard material to be readily fastened and installed at the lipolysis device, thereby facilitating contact with the user's skin.

Meanwhile, the contact plate further includes a heat dissipating plate for dissipating heat generated from the laser diodes 15. That is, since a large amount of heat is generated when laser radiation is radiated from the laser diodes 15 installed at the contact plate 14, the contact plate 14 further includes the heat dissipating plate in order to distribute the heat and cool the contact plate 14. While the contact plate 14 in accordance with an embodiment of the present invention further includes the heat dissipating plate, the contact plate 14 may be formed of a heat dissipating material.

Here, grips 31 for a user to grip the frame 30 by hand are formed at appropriate places on one or both sides of the frame 30. While the frame in accordance with an embodiment of the present invention includes the grips 31 formed at appropriate places on one or both sides of the frame 30, providing that the user can conveniently grip and use the frame 30, the grips 31 may be formed at appropriate places on upper and lower sides of the frame 30.

Meanwhile, it is also possible to further include a positioning means for a doctor or a user to change a position of the frame 30 in vertical and horizontal directions at a rear surface of the frame 30, but a description of this will be omitted. Specifically, a well-known positioning means 35 can be installed at a rear surface of the frame 30 to move the frame 30 having a means for contacting a human body in vertical and horizontal directions at a user's convenience, similar to medical equipment that is freely movable by a doctor. Therefore, the frame 30 can be readily moved to a part of the user's body as required by the user.

Hereinafter, a method or process of using a lipolysis device using a low power laser in accordance with the present invention will be described.

First, a doctor licensed to practice medicine at a medical institution holds grips 31 installed at the frame 30 of the lipolysis device 1 using a low power laser, and moves the lipolysis device 1 to be in close contact with the skin of a patient at a place where fat is to be broken down.

Then, the laser generating unit 10 is driven to generate a laser through the laser diodes 15 and irradiate the skin with the laser.

At this time, the laser with a low output of 10 mW~100 mW is generated through each laser diode 15 of the laser generating unit 10, and passes through a plurality of transparent windows or lenses 13 to be radiated onto the skin where subcutaneous fat is to be broken down.

As described above, the subcutaneous fat is broken down by the laser radiated onto the user's skin in an area such as the abdomen and so on, and the broken down fat is removed from the body by surgical operation.

Here, the lipolysis device 1 using a low power laser in accordance with the present invention uses a red laser together with an infrared laser. The red laser requires an output of 30 mW or more at 635~680 nm, and the infrared laser requires an output of 50 mW or more at 780~980 nm. Hereinafter, the red laser and the infrared laser may be adapted without discrimination.

As described above, each radiation range of the low power laser generated and radiated from each of the laser diodes 15 has an oval shape as shown in FIG. 5 so that there is no overlapping between the radiation ranges and the laser is radiated onto the corresponding contact part only to break down subcutaneous fat.

Figure 7:
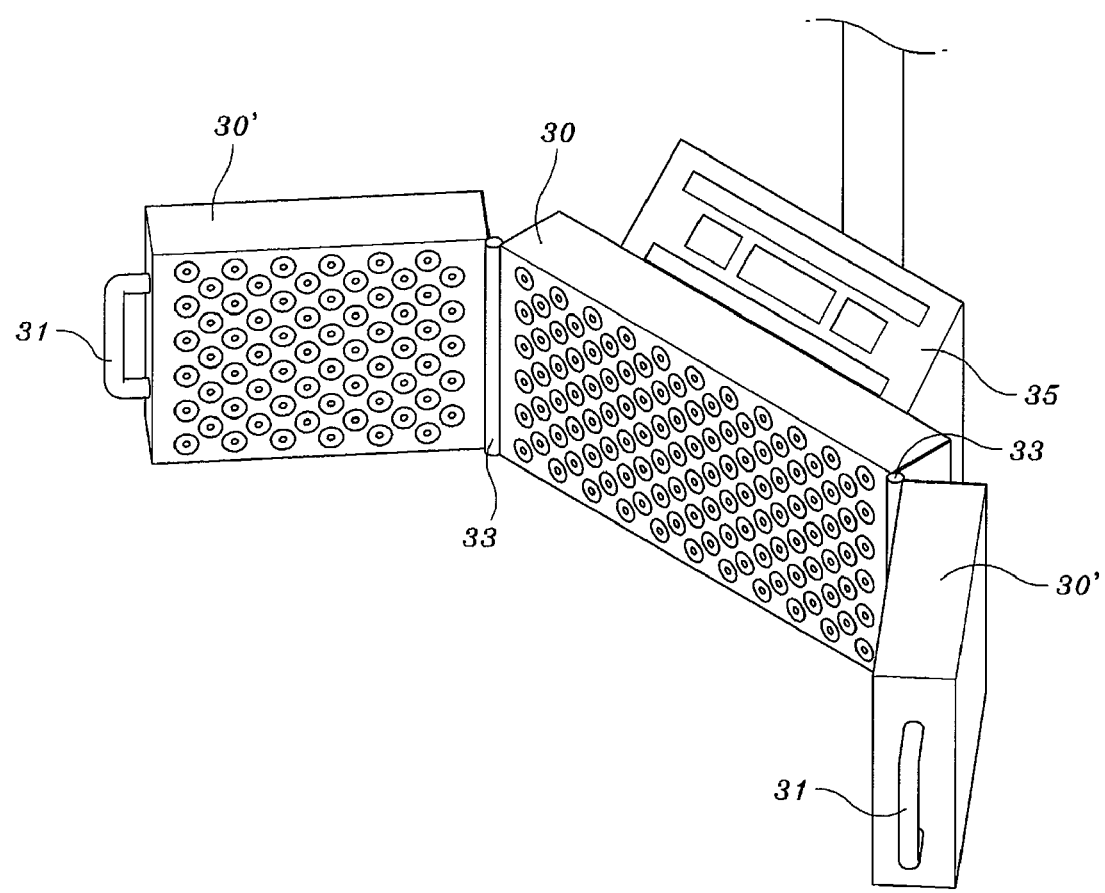
FIG. 7 is a perspective view of an embodiment of a lipolysis device using a low power laser in accordance with the present invention.

FIG. 7 is a perspective view of an embodiment of a lipolysis device using a low power laser in accordance with the present invention, in which several components are different from FIG. 6.

Referring to FIG. 7 together with FIGS. 4 and 5, a lipolysis device 1 using a low power laser in accordance with an embodiment of the present invention includes hinges 33 pivotally installed at both side ends of a frame 30, and other frames 30' are connected to the hinges 33, respectively.

That is, the hinges 33 are installed at both sides of the frame 30 of the lipolysis device 1 using a low power laser, and other frames 30' are connected to the hinges 33, respectively, thereby forming a shape surrounding a user's abdomen or waist.

As described above, the frames 30 and 30' having the laser generating units 10 are continuously and pivotally connected to each other by the hinges 33 so that the frames 30 and 30' can be in three-dimensional contact with the user's abdomen, waist-side, or the like.

While the frame 30 of the embodiment includes the hinges 33 at both sides, and the other frames 30' are connected to the frame 30 by means of the hinges 33, since the other frames 30' include the hinges 33, and the other frames 30' are continuously installed by means of the hinges 33, the lipolysis device can be used to break down subcutaneous fat regardless of the user's body shape.

While the contact plates 14 installed at a front surface of the respective frames 30 and 30' connected by the hinges 33 have a planar shape in the present embodiment, they may be bent into various curved shapes so that the laser can be readily radiated onto the user's abdomen and waist-sides.

In addition, the contact plate 14 may have various shapes such as rectangular, circular, or oval, or may be formed of a flexible material to be manipulated into various shapes.

Figure 8:
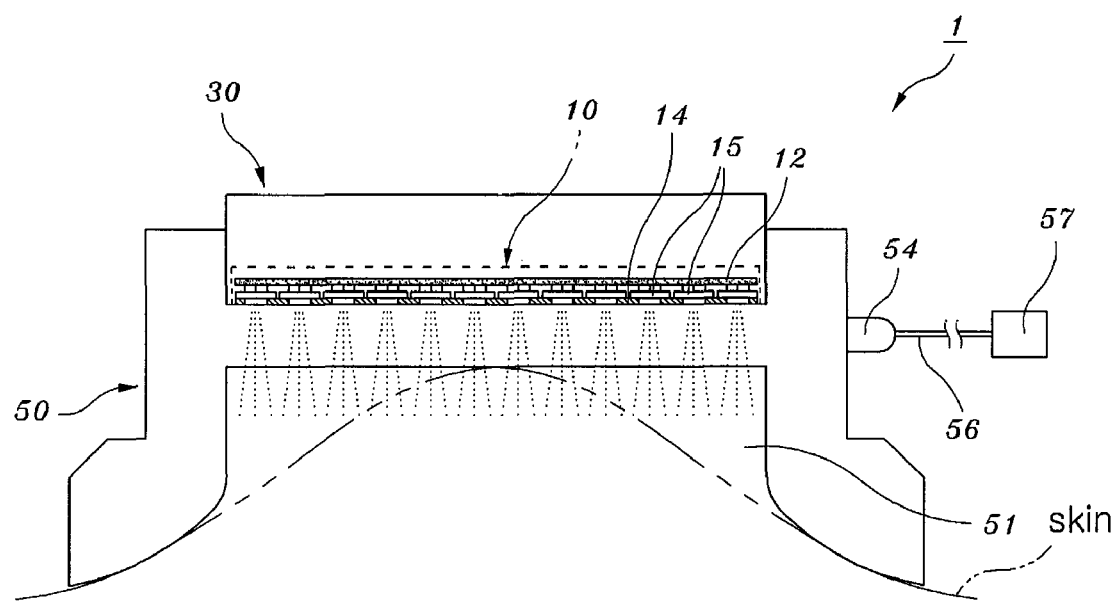
FIG. 8 is a schematic view of another embodiment of a lipolysis device using a low power laser in accordance with the present invention.

FIG. 8 is a schematic view of another embodiment of a lipolysis device using a low power laser in accordance with the present invention.

Referring to FIG. 8 together with FIGS. 4 and 5, a lipolysis device 1 using a low power laser in accordance with an embodiment of the present invention further includes a vacuum suction means 50, in addition to a laser generating unit 10, and a frame 30 for accommodating the laser generating unit 10.

That is, the lipolysis device 1 further includes the vacuum suction means 50, in addition to a printed circuit board (PCB) 12 provided with a power connector 11, a contact plate 14 corresponding to the PCB 12 and having a plurality of transparent windows or lenses 13 disposed on its one surface at predetermined intervals, and a plurality of laser diodes 15 inserted into the respective transparent windows or lenses 13 disposed on the contact plate 14 and electrically connected to the PCB 12.

Here, while the contact plate 14 may further include a heat dissipating plate to radiate heat generated from the laser diodes 15, the contact plate 14 may be formed of a heat dissipating material.

The vacuum suction means 50 has a shape conforming to a shape of the frame and disposed at a front surface of the frame 30, and has a suction port 51 in appropriate contact with a user's skin, a vacuum line 56 connected to the suction port 51 through a vacuum suction part 54, and a vacuum pump 57 connected to the vacuum line 56, thereby forming a predetermined vacuum pressure.

In this process, the vacuum pump 57 sucks air in the suction port 51 in contact with the user's skin through the vacuum suction part 54 to bring the suction port to a predetermined vacuum pressure. The air removed by the vacuum pump 57 is moved through the vacuum suction part 54 and the vacuum line 56.

Figure 9:
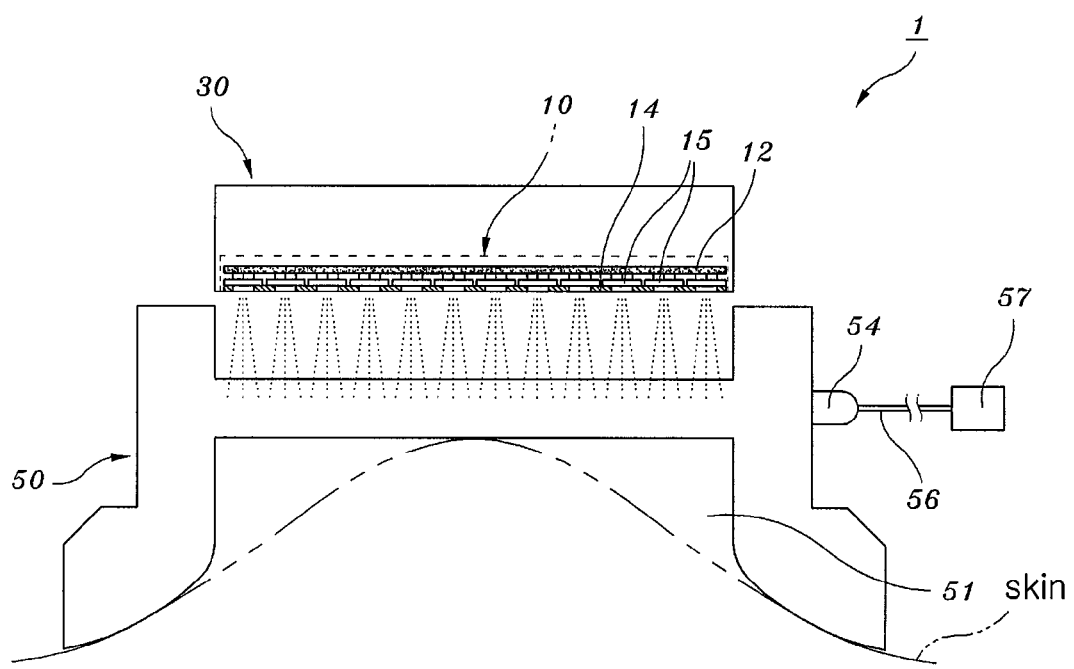
FIG. 9 is a schematic view of an embodiment of a lipolysis device using a low power laser in accordance with the present invention.

While the vacuum suction means 50 of the present embodiment may be integrally formed with the frame 30 at a front surface of the contact plate 14 of the lipolysis device 1 using a low power laser, as shown in FIG. 9, it may alternatively be detachably coupled to the frame 30 of the lipolysis device 1 using a low power laser.

In this process, preferably, the vacuum suction means 50 is detachably coupled to the frame 30 of the lipolysis device 1 using a low power laser by means of fitting or threaded engagement.

In accordance with the above-described structure and shape, it is possible to fasten or separate the vacuum suction means 50 to or from the lipolysis device 1 using a low power laser depending on a doctor or user's need.

Meanwhile, a step (not shown) suitable for close contact with the user's skin is preferably formed at one side periphery of the vacuum suction means 50.

Hereinafter, a method or process of using a lipolysis device using a low power laser in accordance with the present invention will be described.

First, a doctor licensed to practice medicine at a medical institution brings a vacuum suction means of a lipolysis device 1 using a low power laser into close contact with a user's skin for breaking down fat. That is, a suction port 51 of the vacuum suction means 50 is brought into close contact with an appropriate part of the user's skin.

As described above, after the suction port 51 of the vacuum suction means 50 is brought into close contact with the user's skin, the vacuum pump 57 brings the interior of the suction port 51 to a predetermined vacuum pressure so that the skin over the subcutaneous fat to be broken down is in close contact with an inner periphery of the suction port 51.

After the skin covering the subcutaneous fat to be broken down is brought into close contact with an inner periphery of the suction port 51 to be positioned adjacent to the laser generating unit 10, the laser generating unit 10 is driven to generate a laser through the laser diodes 15 and irradiate the skin with the laser.

That is, after attaching the suction port 51 of the vacuum suction means 50 to the user's abdomen, the vacuum pump 57 sucks out the air in the suction port 51 to bring the skin into close contact with the inner surface of the suction port 51, and the laser is radiated onto the skin in an area such as the abdomen to break down subcutaneous fat.

At this time, a low power laser with an output of 10 mW~100 mW is generated through each laser diode 15 of the laser generating unit 10, and the generated laser passes through the transparent windows or lenses 13 to be radiated onto the skin, thereby breaking down subcutaneous fat.

As described above, the subcutaneous fat is broken down by the laser radiated onto the user's skin suctioned by the vacuum suction means 50, and the broken down fat is removed from the body by surgical operation.

In this process, since the subcutaneous fat broken down by the laser generated from the laser diodes 15 is located beneath the skin suctioned in the suction port 51 by means of the vacuum state in the suction port 51 of the vacuum suction means 50, when the vacuumed suction port 51 is moved in a scan manner, the broken down subcutaneous fat moves too.

It is also possible to discharge the subcutaneous fat through the groin region after moving the subcutaneous fat broken down by the laser by the aforementioned method through the suction port 51 of the vacuum suction means 50.

Figure 10:
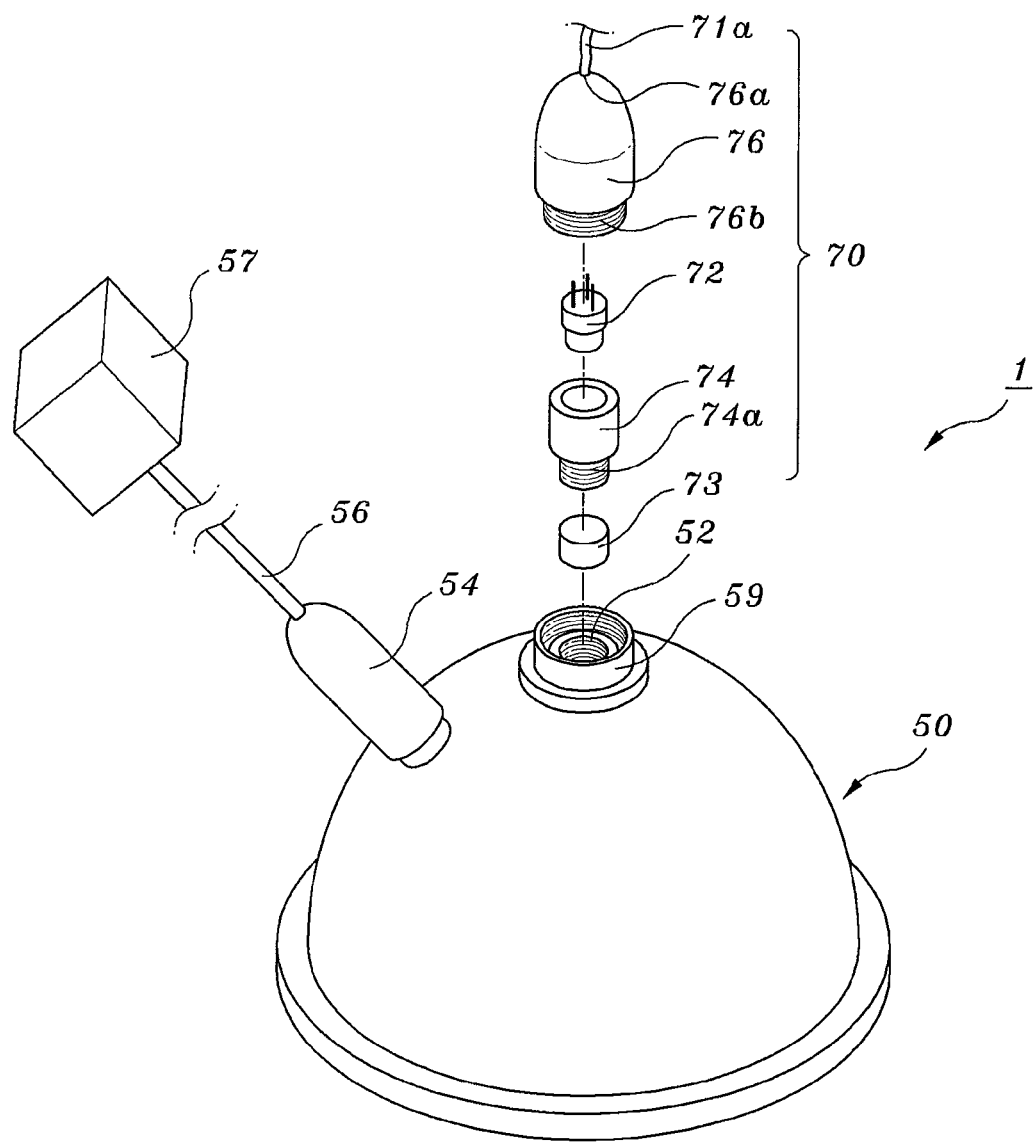
FIG. 10 is an exploded perspective view of another embodiment of a lipolysis device using a low power laser in accordance with the present invention.
Figure 11:
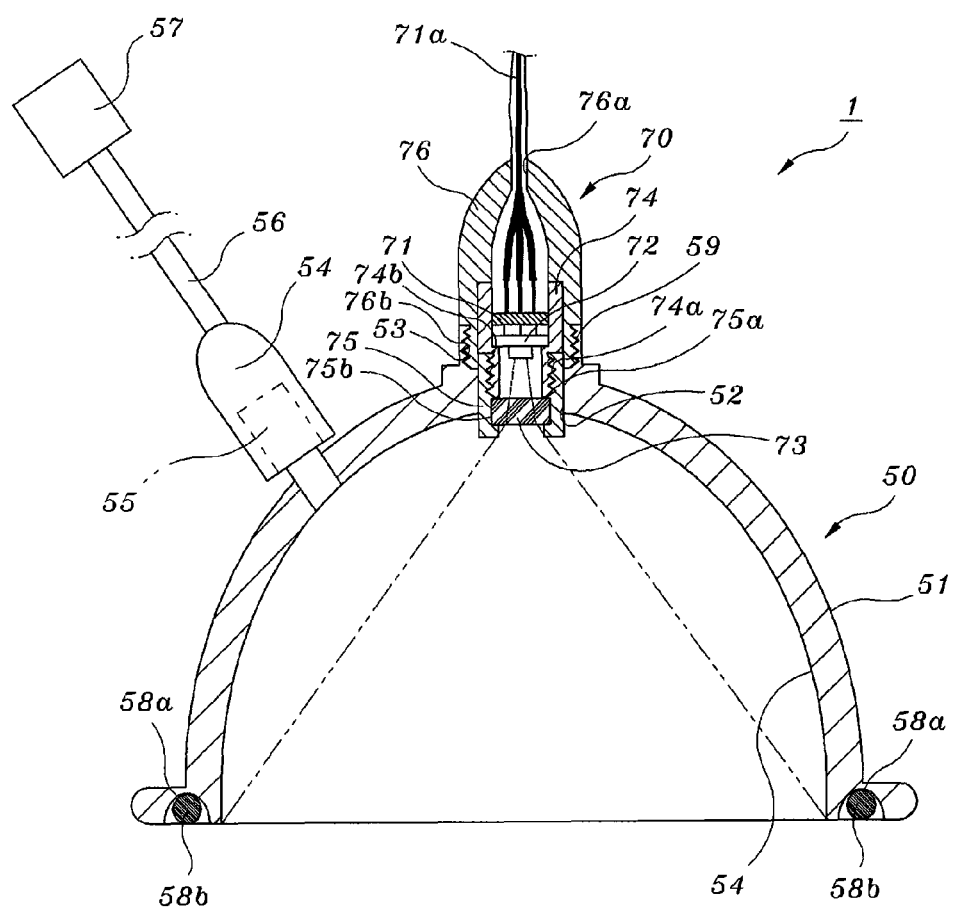
FIG. 11 is a cross-sectional view of an assembly of a vacuum suction means and a laser generating module of a lipolysis device using a low power laser in accordance with the present invention.

FIG. 10 is an exploded perspective view of another embodiment of a lipolysis device using a low power laser in accordance with the present invention, and FIG. 11 is a cross-sectional view of an assembly of a vacuum suction means and a laser generating module of a lipolysis device using a low power laser in accordance with the present invention.

Referring to FIGS. 10 and 11 together with FIGS. 4 and 5, a lipolysis device 1 using a low power laser in accordance with an embodiment of the present invention includes a vacuum suction means 50 and a laser generating module 70.

The vacuum suction means 50 includes a suction port 51 in contact with an appropriate part of a user's skin for breaking down subcutaneous fat, a vacuum line 56 connected to the suction port 51 through a vacuum suction part 54, and a vacuum pump 57 connected to the vacuum line 56 to form a predetermined vacuum pressure.

In this process, the vacuum pump 57 sucks out the air in the suction port 51 in contact with the user's skin through the vacuum suction part 54 to bring the interior of the suction port 51 to a predetermined vacuum pressure, and the air sucked out by the vacuum pump 57 is moved through the vacuum suction part 54 and the vacuum line 56.

Meanwhile, in order to install the laser generating module 70, a coupling part 59 has a coupling hole 52 projecting upward from an upper center of the suction port 51.

The laser generating module 70 includes a PCB 71 for receiving power, a laser diode 72 electrically connected to the PCB 71, a transparent window or lens 73 disposed adjacent to the laser diode 72, upper and lower fixtures 74 and 75 for accommodating the PCB 71, the laser diode 72, and the transparent window or lens 73, which are detachable from each other, and a cover 76 installed outside the upper and lower fixtures 74 and 75.

In addition, a male threaded part 74a and a female threaded part 75a are formed at a lower periphery of the upper fixture 74 and an upper periphery of the lower fixture 75 to be threadedly engaged with each other, a hooking threshold 74b is formed at an inner periphery of the upper fixture 74 to be engaged with the PCB 71, and a groove 75b is formed at a lower periphery of the lower fixture 75 to be engaged with the transparent window or lens 73.

In this process, by fastening and releasing the male threaded part 74a and the female threaded part 75a formed at the upper and lower fixtures 74 and 75, an interval between the laser diode 72 and the transparent window or lens 73 can be adjusted.

Meanwhile, the PCB 71 is connected to a cable 71a to receive power, and an insertion hole 76a for inserting the cable 71a therethrough is formed at an upper part of the cover 76.

In addition, in order to fasten the vacuum suction means 50 and the laser generating module 70 to each other, female and male threaded parts 53 and 76b are formed at an inner upper side of the coupling hole 52 of the suction port 51 and an outer periphery of the cover 76. Further, the upper and lower fixtures 74 and 75 may be formed of a thermal interface material for radiating heat generated from the laser diode 72 of the laser generating module 70.

Meanwhile, the suction port 51 has a manual negative pressure release hole 58 for manually releasing a vacuum or negative pressure in the suction port 51, i.e., by the finger of a doctor or a user.

While the suction port 51 of the present embodiment has a single manual negative pressure release hole 58, providing that the vacuum or negative pressure in the suction port 51 can be readily released, the suction port 51 may have at least two manual negative pressure release holes 58.

In addition, while the manual negative pressure release hole 58 has a circular shape, the manual negative pressure release hole 58 may have various shapes such as oval, rectangular, or the like, and may also have various diameters.

In this process, an annular insertion groove 58a is formed at an end of the suction port 51, and balls 58b are rotatably inserted into the insertion groove 58a. Specifically, in order to readily move the suction port 51 under the vacuum or negative pressure, the annular insertion groove 58a extends from a lower surface of the suction port 51, and the balls 58b are inserted into the insertion groove 58a.

While the suction port 51 of the embodiment has a structure including the annular insertion groove 58a and the plurality of balls 58b rotatably inserted into the groove 58a, under the condition that the suction port 51 can move along the user's skin under the vacuum or negative pressure, the suction port 51 may have various end structures.

Meanwhile, the vacuum suction part 54 connected to the suction port 51 includes an one way valve 55 formed of a check valve, and so on, thereby maintaining the predetermined vacuum pressure in the suction port 51.

In addition, when the air in the suction port 51 is sucked through the vacuum suction part 54, a rhythm mode of repeatedly sucking the air in the suction port 51 at predetermined intervals, and a uniform mode of continuously maintaining the air sucked in the suction port 51, may be operated. Preferably, the user may select the mode.

While the suction port 51 of the present embodiment has a semi-spherical shape, as long as the suction port 51 has a predetermined space for forming a vacuum pressure therein, and the vacuum pressure can be readily formed by the vacuum pump 57, the suction port 51 may have various shapes such as hexahedron, oval, or the like.

In addition, the vacuum suction part 54 of the suction port 51 preferably has a circular or oval end periphery to be in close contact with the user's skin.

Hereinafter, a method or process of using a lipolysis device using a low power laser in accordance with an embodiment of the present invention will be described.

First, a doctor licensed to practice medicine at a medical institution brings the vacuum suction means 50 of the lipolysis device 1 using a low power laser into close contact with the user's skin where subcutaneous fat is to be broken down. That is, the suction port 51 of the vacuum suction means 50 is brought into close contact with an appropriate part of the user's skin such as the face, shoulders, armpits, and so on.

As described above, after the suction port 51 of the vacuum suction means 50 is brought into close contact with the user's skin, the vacuum pump 57 brings the interior of the suction port 51 to a predetermined vacuum pressure so that the skin covering the subcutaneous fat to be broken down is in close contact with an inner periphery of the suction port 51.

After the skin covering the subcutaneous fat to be broken down is brought into close contact with an inner periphery of the suction port 51 to be positioned adjacent to the laser generating module 70, the laser generating module 70 is driven to generate a laser through the laser diodes 72 and irradiate the skin with the laser.

That is, after attaching the suction port 51 of the vacuum suction means 50 to the user's skin in an area such as the face, shoulders, armpits and so on, the vacuum pump 57 sucks the air out of the suction port 51 to bring the skin into close contact with the inner surface of the suction port 51, and the laser is radiated onto the skin to break down subcutaneous fat.

At this time, a low power laser with an output of 10 mW~100 mW is generated through the respective laser diodes 72 of the laser generating unit 10, and the generated laser passes through the transparent windows or lenses 73 to be radiated onto the skin, thereby breaking down subcutaneous fat.

Meanwhile, after the cover 76 is separated from the laser diode 72 of the laser generating module 70, the male threaded part 74a and the female threaded part 75a formed at the upper and lower fixtures 74 and 75 are adjusted to adjust an interval between the laser diode 72 and the transparent window or lens 73, preferably, at the beginning of the installation and treatment.

As described above, the subcutaneous fat is broken down by the laser radiated onto the user's skin suctioned by the vacuum suction means 50, and the broken down subcutaneous fat is removed from the body by surgical operation.

In this process, since the subcutaneous fat broken down by the laser generated from the laser diodes 72 is located beneath the skin suctioned in the suction port 51 by means of the vacuum state in the suction port 51 of the vacuum suction means 50, if the vacuumed suction port 51 is moved on the skin by means of rotation of the balls 58b inserted into the insertion groove 58a formed at the end of the suction port 51 in a scan manner, the broken down subcutaneous fat can be discharged through the groin, in which lymphatic vessels are abundant.

It is preferable to discharge the subcutaneous fat from the body after moving the subcutaneous fat broken down by the laser using the aforementioned method through the suction port 51 of the vacuum suction means 50.

Meanwhile, manually opening or closing the manual negative pressure release hole 58 formed at the suction port 51 of the vacuum suction means 50 by the doctor or the user, the vacuum or negative pressure in the suction port 51 can be manually released, and therefore, the doctor or the user can readily set or release the vacuum or negative pressure formed in the suction port 51.

When the vacuum suction means 50 is used on the user's head, blood circulation as well as hair growth can be promoted.

Figure 12:
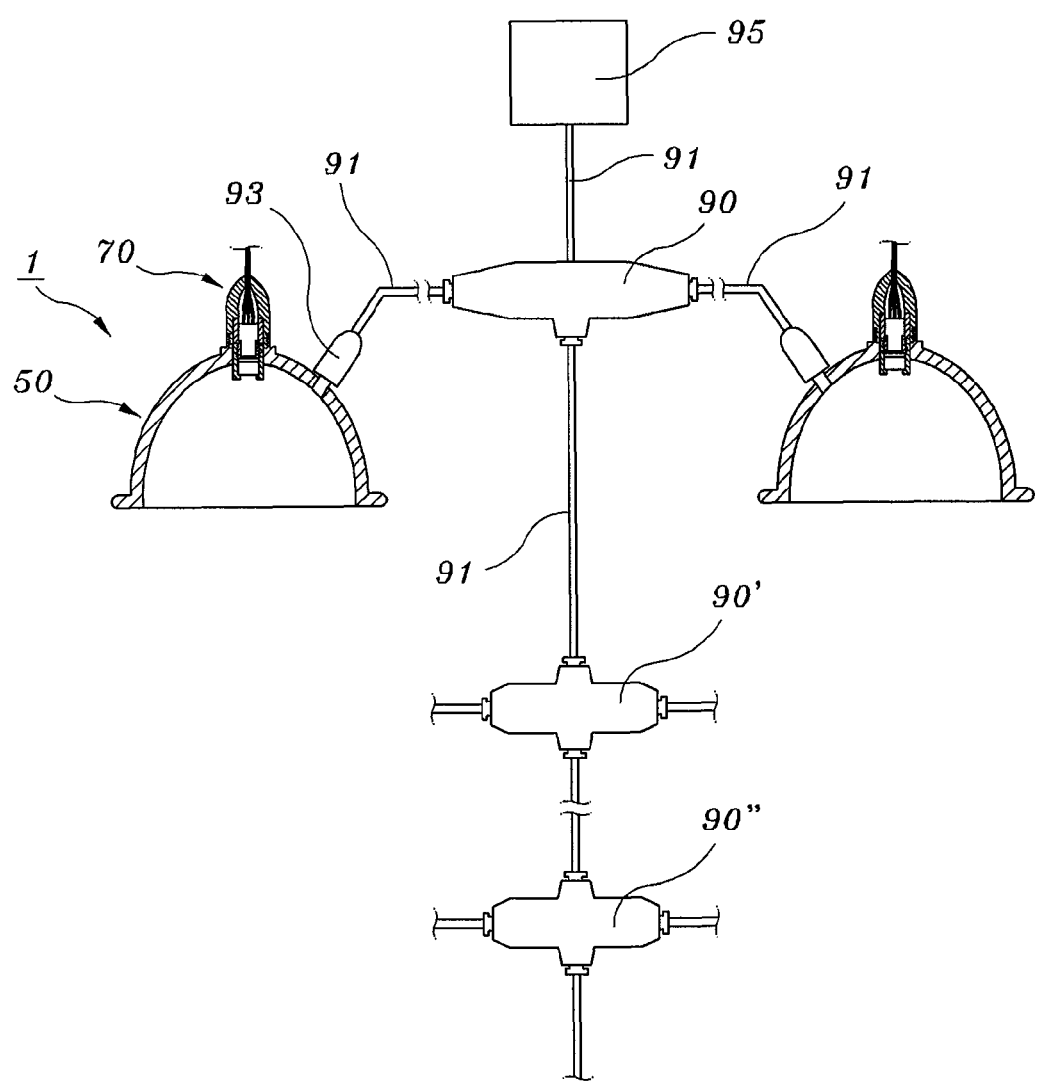
FIG. 12 is a schematic view of a lipolysis device using a low power laser in accordance with the present invention.

Meanwhile, as shown in FIG. 12, a relay may be installed at an appropriate place at a vacuum suction means having a laser generating module. Describing with reference to FIGS. 10 and 11, the relay 90 is installed at an appropriate place at the vacuum suction means 50 having the laser generating module 93, and branches off into a plurality of connection vacuum line 91 having the vacuum suction ports 93. In addition, the relay 90 is connected to the vacuum suction means 50 through the vacuum suction part 93, and another vacuum line 91 connected to another vacuum suction part 93 having the laser generating module 70 is connected to another vacuum suction part 93 of the vacuum suction means 50 having another laser generating module 70.

As described above, a plurality of vacuum suction means 50 each having laser generating module 70 are connected to the relay 90 through the connection vacuum lines 91 so that the vacuum suction means 50 can be in contact with a predetermined area of skin where subcutaneous fat is to be broken down.

In this process, the connection vacuum line 91 for connecting the vacuum suction means 50 having the laser generating module 70 and the relay 90 through the vacuum suction part 93 has a length that may be variably adjusted by the user, thereby enabling many people to use the lipolysis device.

For this purpose, any one of the connection lines 91 branching off from the relay 90 may be connected to the vacuum pump 95 for forming a predetermined vacuum pressure in the suction port 51, and another connection vacuum line 91 may be another relay 90.

As described above, the relay 90 for connecting the plurality of vacuum suction means 50 having the laser generating modules 70 may be connected to another relay 90' through the connection vacuum line 91 so that the plurality of vacuum suction means 50 are in contact with the user's skin.

Although the present invention has been described with reference to certain exemplary embodiments thereof, it will be understood by those skilled in the art that a variety of modifications may be made therein without departing from the spirit or scope of the present invention defined by the appended claims and their equivalents.

What is claimed is:

1. A lipolysis device comprising:
a laser generator having:
a printed circuit board (PCB) provided with a power connector;
a contact plate corresponding to the PCB and having a plurality of transparent windows or lenses uniformly disposed at one side surface, the contact plate being provided to be in contact with skin of a user; and
a plurality of laser diodes inserted into the respective transparent windows or lenses disposed on the contact plate and electrically connected to the PCB for irradiating a user with low power laser radiation to break down subcutaneous fat of the user; and
a frame for accommodating the laser generator therein,
wherein the contact plate further comprises a heat dissipating plate for dissipating heat generated from the laser diodes and for cooling the contact plate.

2. The lipolysis device according to claim 1, wherein each of the laser diodes has an output of 10 mW-100 mW.

3. The lipolysis device according to claim 1, wherein the contact plate is bent to have an oval surface suitable for contact with the skin of the user, and the frame for accommodating the contact plate is bent to have an oval surface corresponding to the contact plate.

4. The lipolysis device according to claim 1, wherein the frame has grips formed at appropriate places on one or both sides thereof.

5. The lipolysis device according to claim 1, wherein other frames are connected to hinges pivotally installed at both ends of the frame, respectively.

* * * * *